US012791471B2

(12) United States Patent
Stone et al.

(10) Patent No.: US 12,791,471 B2
(45) Date of Patent: Nov. 10, 2026

(54) MOISTURE AND ORGANIC MATTER PREDICTION USING NEAR INFRARED LIGHT

(71) Applicant: MIRATERRA INC., Lewes, DE (US)

(72) Inventors: David C. Stone, San Francisco, CA (US); Sheng-Yang Matthew Goh, San Francisco, CA (US); Michael Wiest, San Diego, CA (US); Bradly R. Roetman, Ames, IA (US); Terry S. Nederhoff, Ames, IA (US)

(73) Assignee: MIRATERRA INC., Lewes, DE (US)

( * ) Notice: Subject to any disclaimer, the term of this patent is extended or adjusted under 35 U.S.C. 154(b) by 535 days.

(21) Appl. No.: 17/833,210

(22) Filed: Jun. 6, 2022

(65) Prior Publication Data

US 2023/0393062 A1 Dec. 7, 2023

(51) Int. Cl.

| | |
|---|---|
| ***G01N 21/3563*** | (2014.01) |
| ***G01N 21/31*** | (2006.01) |
| ***G01N 21/35*** | (2014.01) |
| ***G01N 21/3554*** | (2014.01) |
| ***G01N 21/359*** | (2014.01) |
| ***G01N 33/24*** | (2006.01) |

(Continued)

(52) U.S. Cl.

CPC ..... *G01N 21/3563* (2013.01); *G01N 21/3554* (2013.01); *G01N 21/359* (2013.01); *G01N 33/24* (2013.01); *G06N 3/04* (2013.01); *G01N 21/31* (2013.01); *G01N 21/314* (2013.01); *G01N 21/35* (2013.01); *G01N 2201/1296* (2013.01); *G06N 3/0464* (2023.01); *G06N 3/048* (2023.01); *G06N 3/09* (2023.01)

(58) Field of Classification Search

CPC .......... G01N 21/3563; G01N 21/3554; G01N 21/359; G01N 33/24; G01N 21/31; G01N 21/35; G01N 21/314; G01N 2201/1296; G06N 3/04; G06N 3/09; G06N 3/0464; G06N 3/048

See application file for complete search history.

(56) References Cited

U.S. PATENT DOCUMENTS

2021/0181176 A1 * 6/2021 Acedo .................... G01N 33/24

FOREIGN PATENT DOCUMENTS

CN 114034684 A * 2/2022
WO WO-2018126033 A1 * 7/2018 ............... C12Q 1/06

OTHER PUBLICATIONS

Mirzaei et al. (Minimising the effect of moisture on soil property prediction accuracy using external parameter orthogonalization, Soil and Tillage Research, vol. 215, 2022, 105225, ISSN 0167-1987, https://doi.org/10.1016/j.still.2021.105225.) (Year: 2021).*

(Continued)

*Primary Examiner* — Christian T Bryant

(74) *Attorney, Agent, or Firm* — FBT Gibbons LLP

(57) ABSTRACT

A method includes receiving a value for a spectral band identified from a soil sample and inputting the value for the spectral band to a system that predicts a percentage of carbon matter in the soil sample using values of spectral bands. The ability of the system to correctly predict the percentage of carbon matter in the soil sample is improved by further inputting a humidity level to the system wherein the humidity level indicates an amount of ambient moisture present when the value for the spectral band was identified.

16 Claims, 7 Drawing Sheets

(51) Int. Cl.
*G06N 3/04* (2023.01)
*G06N 3/0464* (2023.01)
*G06N 3/048* (2023.01)
*G06N 3/09* (2023.01)

(56) References Cited

OTHER PUBLICATIONS

Shen et al. (Hyperspectral Estimation of Soil Organic Matter Content using Different Spectral Preprocessing Techniques and PLSR Method. Remote Sens. 2020, 12, 1206. https://doi.org/10.3390/rs12071206) (Year: 2020).*

Wikipedia ("Convolutional neural network." Wikipedia, The Free Encyclopedia. Wikipedia, The Free Encyclopedia, May 24, 2022.) (Year: 2022).*

Gad (Beginners Ask âHow Many Hidden Layers/Neurons to Use in Artificial Neural Networks?â, Towards Data Science, Jun. 27, 2018) (Year: 2018).*

Chen et al. (Convolutional neural network model for soil moisture prediction and its transferability analysis based on laboratory Vis-NIR spectral data,International Journal of Applied Earth Observation and Geoinformation, vol. 104, 2021, 102550, ISSN 1569-8432) (Year: 2021).*

Alexakis et al. (Integrated Use of Satellite Remote Sensing, Artificial Neural Networks, Field Spectroscopy, and GIS in Estimating Crucial Soil Parameters in Terms of Soil Erosion. Remote Sens. May 9, 2019, 11, 1106. https://doi.org/10.3390/rs11091106) (Year: 2019).*

Fernandes et al. (Estimation of soil organic matter content by modeling with artificial neural networks, Geoderma, vol. 350, Sep. 15, 2019, pp. 46-51, ISSN 0016-7061, https://doi.org/10.1016/j.geoderma.2019.04.044.) (Year: 2019).*

Ge et al., A primer on soil analysis using visible and near-infrared (vis-NIR) and mid-infrared (MIR) spectroscopy, Food and Agriculture Organization of the United Nations, 28 pages, 2022.

* cited by examiner

MOISTURE AND ORGANIC MATTER PREDICTION USING NEAR INFRARED LIGHT

BACKGROUND

Spectroradiometers apply light to a sample and measure the amplitude of different spectral bands reflected from the sample. Spectral bands that are absorbed by the sample have a low reflected amplitude.

Spectroradiometers have been used in the past to predict a percentage of organic matter in a soil sample. In such systems, wavelengths of light that are absorbed by organic matter are identified and the amount of light at those wavelengths that is absorbed by a sample is used to calculate the percentage of organic matter in the sample.

There are many challenges to correctly predicting organic matter percentages using spectroradiometers. First, lumps in the soil sample cast shadows across the sample. These shadows affect the amount of light that is absorbed by the sample thereby degrading the accuracy of the organic matter prediction. To address this, the prior art grinds the soil sample to a uniform texture before the test.

Second, there is an overlap in some of the wavelengths of light that water and organic matter absorb. As a result, a wetter soil sample will indicate the presence of more organic matter than a dry sample even when the two samples contain the same amount of organic matter. To address this, the art dries soil samples before testing them to remove moisture from the soil samples.

Even with these additional preprocessing steps, existing spectroradiometer systems do not provide fully accurate organic matter predictions.

The discussion above is merely provided for general background information and is not intended to be used as an aid in determining the scope of the claimed subject matter. The claimed subject matter is not limited to implementations that solve any or all disadvantages noted in the background.

SUMMARY

A method includes receiving a value for a spectral band identified from a soil sample and inputting the value for the spectral band to a system that predicts a percentage of carbon matter in the soil sample using values of spectral bands. The ability of the system to correctly predict the percentage of carbon matter in the soil sample is improved by further providing a measured humidity level to the system wherein the humidity level indicates an amount of ambient moisture present when the value for the spectral band was identified.

In accordance with a further embodiment, a computing device includes a memory containing parameters representing a neural network and a processor using the parameters of the neural network stored in the memory to form the neural network. The neural network includes an input layer receiving spectral band values determined from a soil sample and an ambient humidity value representing ambient humidity present when the spectral band values were determined. The neural network further includes at least one hidden layer connected to the input layer and an output layer indicating an organic matter percentage for a soil sample.

In accordance with a still further embodiment, a method includes placing an unprocessed soil sample in a spectroradiometer and recording values for spectral bands generated by the spectroradiometer from the unprocessed soil sample. A humidity level for air proximate to the spectroradiometer is recorded and the recorded values for the spectral bands and the recorded value for the humidity level are provided to a processing unit to obtain a percentage of organic material in the soil sample.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Embodiments described below improve systems that use spectral values to predict the percentage of organic matter and the moisture content in a soil sample. In particular, the embodiments improve neural networks that use spectral values to predict the organic matter percentage and moisture content. The improvements to the neural network are such that the soil sample does not have to be processed before being placed in a spectroradiometer for spectral analysis. Thus, the soil sample does not have to be ground or dried before being analyzed.

Figure 1:
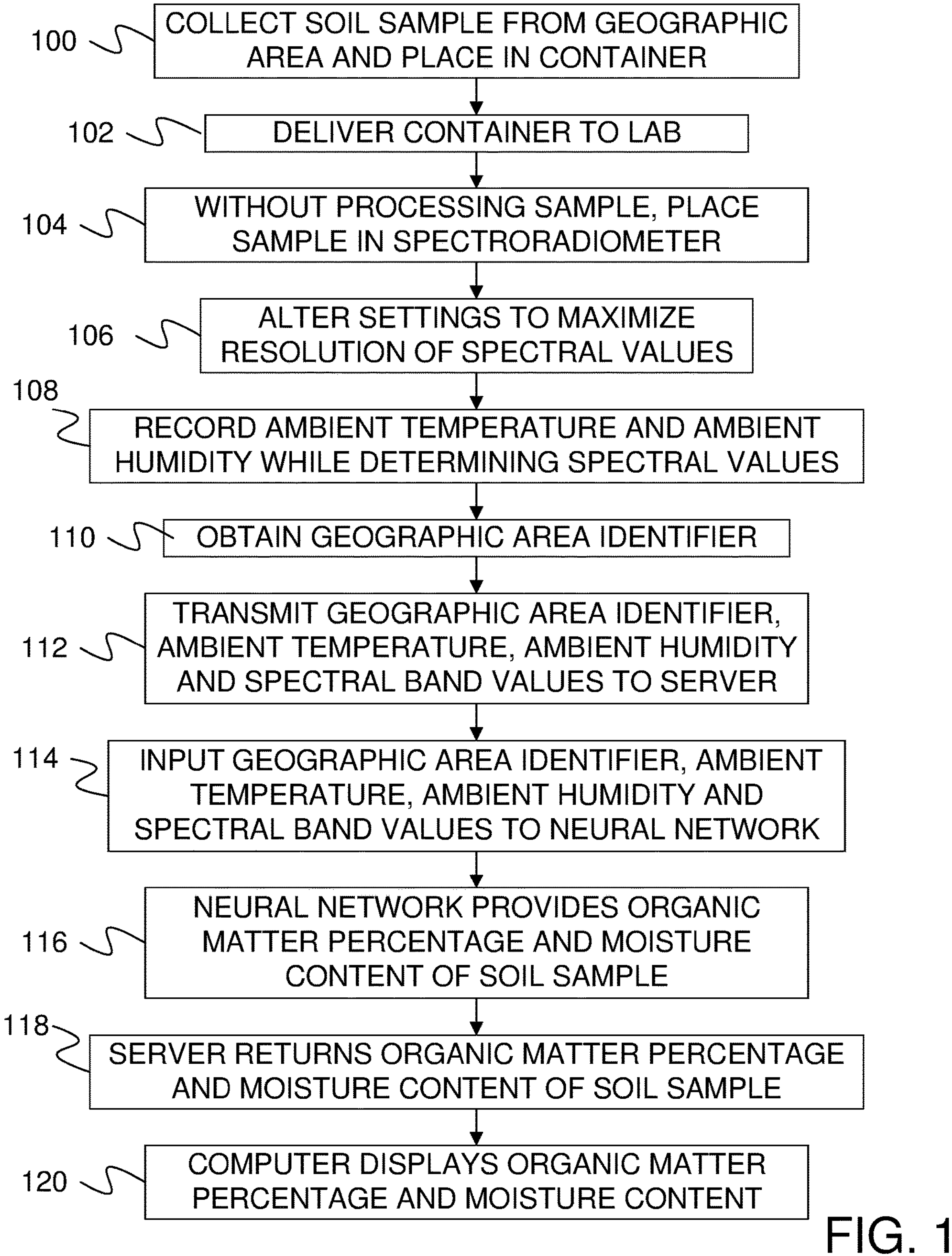
FIG. 1 provides a flow diagram of a method of improving a neural network's ability to predict organic matter percentages and moisture content of a soil sample using spectral values.

FIG. 1 provides a flow diagram of a method for improving systems that predict organic matter percentages and moisture content in a soil sample. In step 100, a soil sample is collected from a field located in a geographic area. Collecting the soil sample involves removing soil from the ground and placing the soil directly into a container, such as a bag. Preferably, the bag is sealed to maintain the moisture content of the soil. No processing needs to be done to the soil before or after it is placed in the bag. In particular, the soil does not have to be ground or sifted before being placed in the bag.

In step 102, the bag containing the soil sample is delivered to a lab for testing. At step 104, a portion of the soil sample is placed in a spectroradiometer (also referred to as a spectrophotometer or spectrometer). In removing the sample from the bag and placing it in the spectroradiometer, no processing is performed on the sample. In particular, the sample is not ground, sifted nor dried before being placed in the spectroradiometer. This greatly reduces the amount of work that must be performed when testing a sample for organic matter and moisture.

Figure 2:
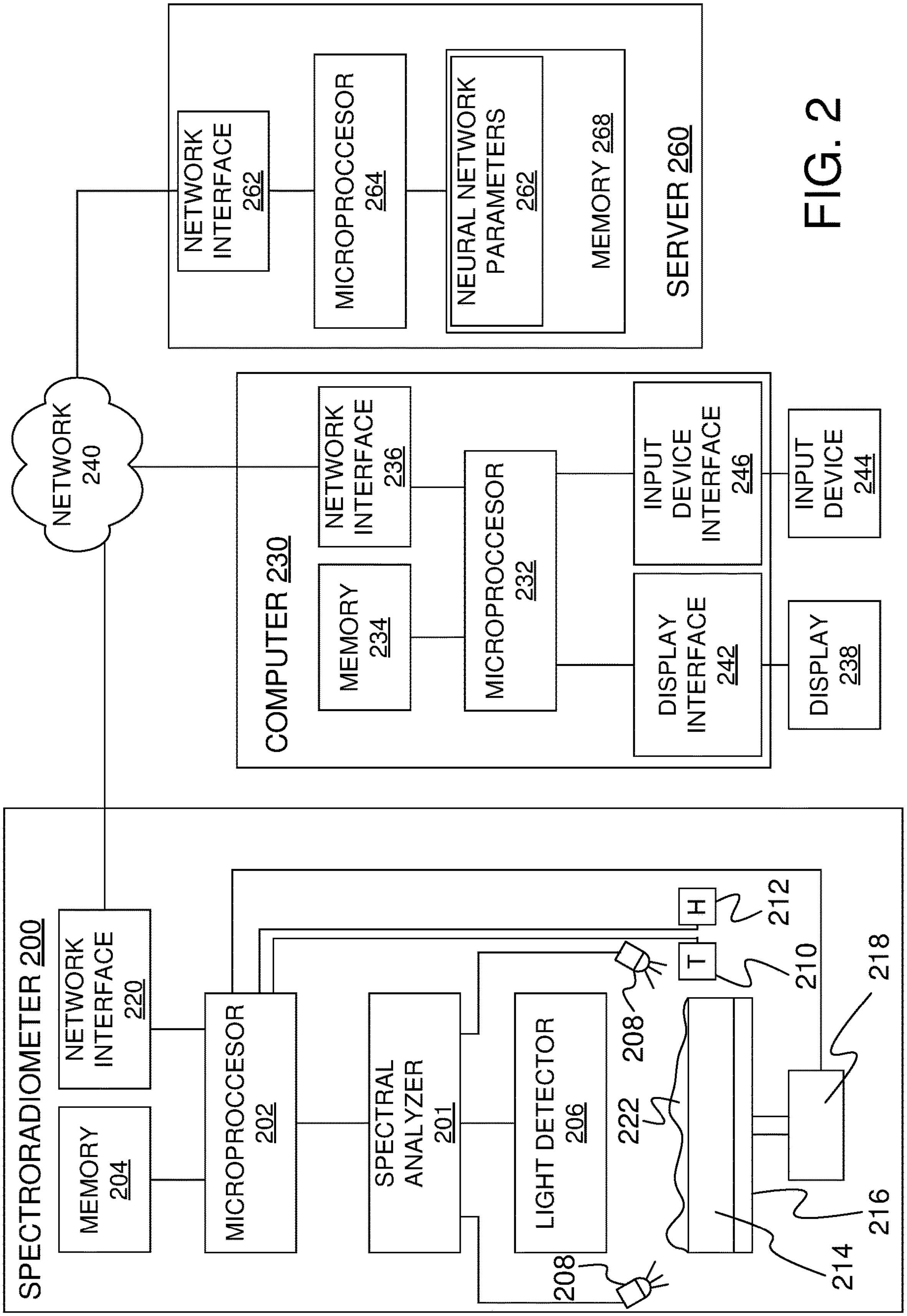
FIG. 2 provides a block diagram of a system for improving a neural network's ability to predict organic matter percentages and moisture content of a soil sample using spectral values.

FIG. 2 provides a block diagram of a system containing a spectroradiometer 200 consisting of spectral analyzer 201, a microprocessor 202, a memory 204, a light detector 206, light emitters 208, a temperature sensor 210, a humidity sensor 212, a sample cup 214, a turntable 216, a motor 218, and a network interface 220.

Microprocessor 202 is connected to network interface 220 and communicates with other computing devices on a network 240 through network interface 220. Microprocessor 202 is also connected to memory 204 and is able to store and retrieve data, configuration settings and instructions from memory 204.

Spectral analyzer 201 is connected to microprocessor 202, light detector 206 and light emitters 208. Spectral analyzer 200 receives configuration settings and instructions from microprocessor 202 and returns the results of spectral analyses to microprocessor 202. Spectral analyzer 201 also provides control signals to light emitters 208 to cause them to emit light during spectral analysis and receives electrical signals from light detector 206 representing the light detected at various spectral bands during spectral analysis.

Microprocessor 202 is also connected to motor 218 and is able to control the rotation of motor 218. During spectral analysis, microprocessor 202 activates motor 218 thereby causing motor 218 to rotate turntable 216 and sample cup 214.

Temperature sensor 210 and humidity sensor 212 detect the ambient conditions near sample cup 214. In particular, temperature sensor 210 detects the temperature of the air near sample cup 214 and humidity sensor 212 senses the amount of moisture in the air near sample cup 214. Temperature sensor 210 and humidity sensor 212 provide analog or digital signals to microprocessor 202 that are indicative of the sensed temperature and humidity, respectively.

When spectroradiometer 200 is used in the method of FIG. 1, step 104 involves placing a soil sample 222 in sample cup 214 and then placing sample cup 214 on turntable 216. After soil sample 222 has been placed in spectroradiometer 200, configuration settings for spectroradiometer 200 are adjusted to maximize the resolution of the spectral values provided by spectral analyzer 201 at step 106. In accordance with one embodiment, the configuration settings are adjusted using a computer 230 connected to spectroradiometer 200 through network 240.

Computer 230 includes a microprocessor 232, a memory 234, a network interface 236, a display 238, a display interface 242, an input device 244 and an input device interface 246. Microprocessor 232 is connected to memory 234 and is able to read and write data and instructions to and from memory 234. Microprocessor 232 is also connected to network interface 236 and is able to communicate with other devices through network interface 236, including spectroradiometer 200 and a server 260. Microprocessor 232 displays user interfaces on display 238 by sending signals through display interface 242 and is able to receive input signals from input device 244 through input device interface 246. In accordance with one embodiment, input device 244 is a keyboard. In other embodiments, display 238 is a touch screen and microprocessor 232 is able to receive input signals from display 238 through display interface 242.

After placing the sample 222 in spectroradiometer 200, a user of computer 230 selects a control displayed in a user interface provided by microprocessor 232 on display 238. In accordance with one embodiment, the control allows the user to initiate a spectral analysis of the sample in spectroradiometer 200. Based on the user's input, microprocessor 232 sends an instruction to microprocessor 202 of spectroradiometer 200 to perform a spectral analysis. In response, microprocessor 202 sends control signals to motor 218 to cause it to start rotating turntable 216 and sample cup 214. Microprocessor 202 then instructs spectral analyzer 201 to perform a spectral analysis of sample 222. During the spectral analysis, spectral analyzer 201 causes light emitters 208 to emit light across a broad spectrum. In one embodiment, the broad spectrum includes visible and near infrared light. Light reflected by soil sample 222 passes to light detector 206, which includes a diffraction grating and an array of light detector elements. The diffraction grating separates the reflected light into different spectral bands and directs each band onto one or more light detector elements. Each light detector element generates an electrical signal that indicates the amount of light incident on the detector element and returns that electrical signal to spectral analyzer 200. Spectral analyzer 200 integrates each electrical signal over an integration period to determine a total amount of light incident on each detector during the integration period. Since each detector element is associated with a respective spectral band, spectral analyzer 200 is able to determine an amount of light reflected from the sample for each spectral band. Spectral analyzer 200 then either sends the amount of reflected light at each spectral band or the amount of light absorbed by the sample at each spectral band to microprocessor 202. The amount of light absorbed or the amount of light reflected for a particular spectral band is referred to herein as a spectral value. In accordance with one embodiment, the amount of light absorbed at each spectral band is determined by subtracting the amount of reflected light at the spectral band from a maximum amount of light reflected for any spectral band.

Each spectral band contains a continuous segment of different wavelengths of light. The number of spectral bands, the width of each band and any separation between the bands is typically fixed in the spectroradiometer or can be adjusted through configuration settings.

Microprocessor 202 returns the spectral values it receives from spectral analyzer 200 to microprocessor 232, which then graphs the spectral values on display 238 with the amount of light reflected or absorbed shown along one axis and the wavelength of light shown along the other axis. The user then reviews the graph to determine how the integration period should be adjusted to maximize the resolution. For example, if any part of the graph appears to be flattened due to exceeding the maximum amount of light that spectroradiometer 200 can detect, the integration period needs to be shortened. On the other hand, if the maximum value shown in the graph is less than the maximum amount of light that spectroradiometer 200 can detect, the integration period is increased so as to increase the resolution of the spectral values. Step 106 may be repeated in an iterative fashion until the integration period provides the desired resolution.

After the configuration settings have been adjusted, the user requests the organic matter content or moisture content of sample 222 by selecting a control displayed in a user interface on display 238. In response, microprocessor 232 sends an instruction to microprocessor 202 to perform a spectral analysis of sample 222 while also recording the ambient temperature and ambient humidity. At step 108, microprocessor 202 of spectroradiometer 200 sends control signals to motor 218 to cause it to start rotating turntable 216 and sample cup 214. Microprocessor 202 then instructs spectral analyzer 201 to perform a spectral analysis of sample 222. Spectral analyzer 201 performs the spectral analysis in the same manner as discussed above. Upon receiving the spectral values from spectral analyzer 201, microprocessor 202 records the ambient temperature provided by temperature sensor 210 and the ambient humidity provided by humidity sensor 212. Microprocessor 202 then returns the spectral values, the ambient temperature and the ambient humidity to microprocessor 232.

At step 110, microprocessor 232 displays a user interface on display 238 to request a latitude and longitude where the sample was taken from. In accordance with one embodiment, the latitude and longitude are converted into one of the Major Land Resource Areas set out by the United States Department of Agriculture by microprocessor 232. In other embodiments, the geographic area is any designation that groups soils of similar parent material that experience similar climatic conditions together. In response to the request, a user selects or enters an identifier for the geographic area so that microprocessor 232 receives the identifier.

At step 112, microprocessor 232 sends the identifier for the geographic area, the ambient temperature value, the ambient humidity value and the spectral values for the spectral bands to server 260 as part of a request for the organic matter percentage and moisture content of soil sample 222. The request is sent through network interface 236 and network 240 to a network interface 262 in server 260. Network interface 260 forwards the request to a microprocessor 264 in server 260.

Upon receiving the request, microprocessor 264 uses neural network parameters 266 stored in a memory 268 of server 260 to implement a neural network. At step 114, microprocessor 264 applies the spectral values as inputs to the neural network. In addition, the microprocessor improves the ability of the neural network to predict the organic matter percentage and the moisture content of the soil by also inputting the identifier for the geographic area, the ambient temperature value and the ambient humidity value to the neural network.

Using the spectral values, the geographic area, the ambient temperature and the ambient humidity, the neural network implemented by microprocessor 264 identifies an organic matter percentage in soil sample 222 and a moisture content in soil sample 222 at step 116. Microprocessor 264 then returns the organic matter percentage and the moisture content to microprocessor 232 at step 118. At step 120, microprocessor 232 displays the organic matter percentage and moisture content on display 238.

Figure 3:
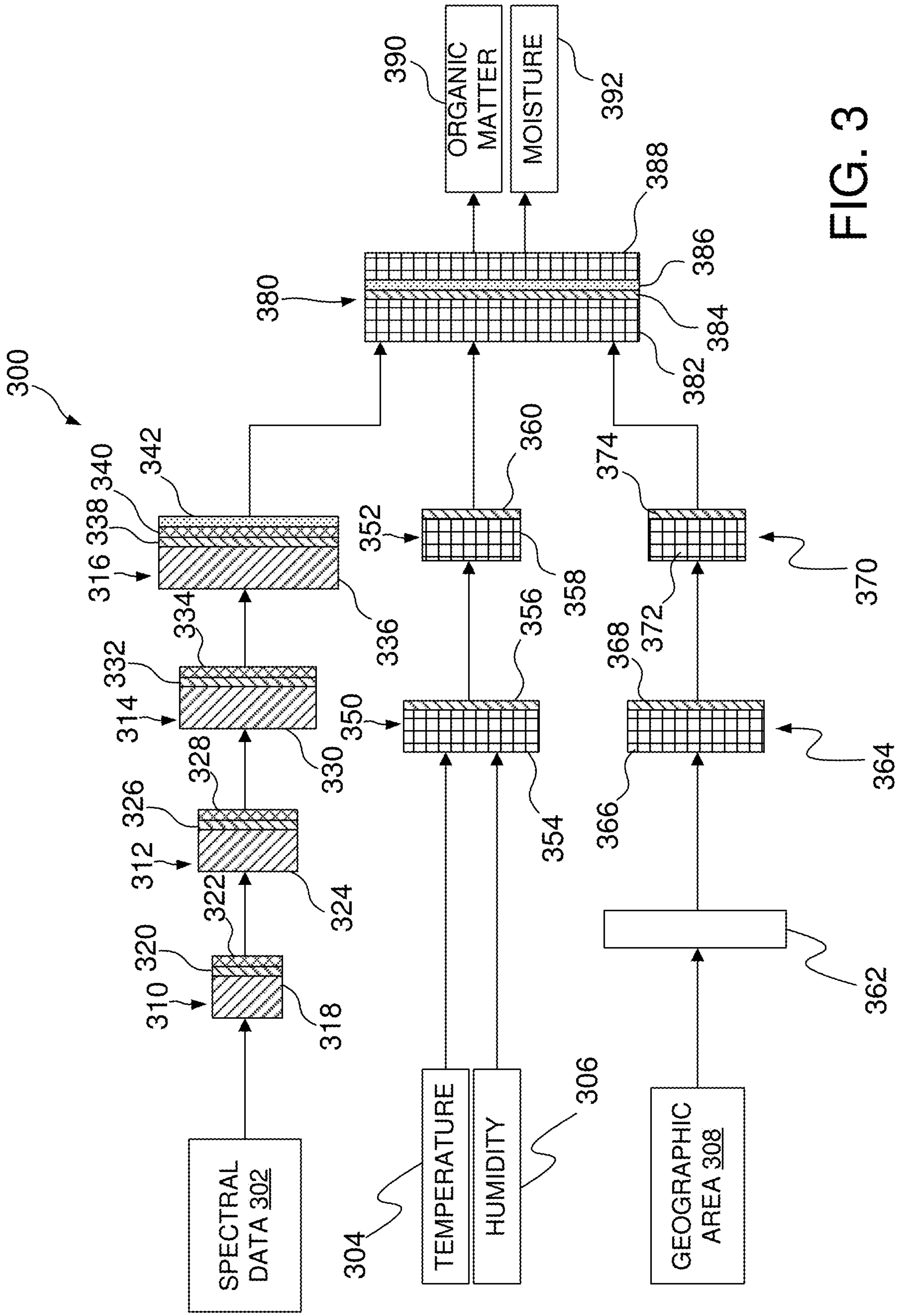
FIG. 3 provides a block diagram of one embodiment of a neural network.

FIG. 3 provides a block diagram of one embodiment 300 of the neural network implemented by microprocessor 264. Neural network 300 receives spectral data 302, temperature value 304, humidity value 306 and geographic area 308. Spectral data 302 consists of the spectral values for the collection of spectral bands. In accordance with one embodiment, approximately 1700 spectral values are in spectral data 302. Spectral data 302 is input to an initial stage 310 that consists of a 1-D convolutional layer 318, followed by a ReLU layer 320 that is followed by a max pooling layer 322. Convolution layer 318 implements a one-dimensional filter or kernel that combines the spectral values of multiple spectral bands into a single value at each of number of positions along the spectrum of spectral data 302. The number of spectral values between the positions is known as the stride and the number of spectral values that are combined at each position is the kernel size. In accordance with one embodiment, the stride and kernel size are selected such that the kernel at each position overlaps at least one other kernel. ReLU layer 320 sets any negative values in the outputs of 1-D convolution layer 318 to zero and max pooling layer 322 selects a largest value from groupings of outputs from ReLU layer 320.

The output of initial stage 310 is provided to a second stage 312, which consists of a 1-D convolution layer 324, followed by a ReLU layer 326 that is followed by a max pooling layer 328. In accordance with one embodiment, thirty-two values are output from initial stage 310 to second stage 312. The output of max pooling layer 328 is input to a third stage 314 consisting of a 1-D convolution layer 330, followed by a ReLU layer 332 that is followed by a max pooling layer 334. In accordance with one embodiment, sixty-four values are output from max pooling layer 328 to third stage 314. The output of max pooling layer 334 is input to fourth stage 316, which consists of a 1-D convolution layer 336, followed by an ReLU layer 338 that is followed by a max pooling layer 340. In accordance with one embodiment, one hundred twenty-eight values are output from max pooling layer 334 to fourth stage 316.

Stages 310, 312, 314 and 316 identify groupings of spectral values that are significant in identifying the organic matter percentage and/or moisture content of a soil sample.

Ambient temperature value 304 and ambient humidity value 306 from the spectroradiometer are input to an initial stage 350 consisting of a fully connected layer 354 followed by a ReLU layer 356. In accordance with one embodiment, ReLU layer 356 produces one hundred twenty-eight output values. The output values of ReLU layer 356 are input to a second stage 352 consisting of a fully connected layer 358 followed by an ReLU layer 360. Initial stage 350 and second stage 352 convert temperature value 304 and humidity value 306 into values that can be used with spectral data 302 and geographic area 308 to determine the organic matter percentage and moisture content of a soil sample.

Geographic area 308 is encoded into a vector using one-hot encoder 362. In accordance with one embodiment, geographic area 308 is a label designating one of the Major Land Resource Areas and one-hot encoder 362 generates a vector that has a bit position for each Major Land Resource Area, with the bit position of the Major Land Resource Area of the input set to one and all other bit positions set to zero.

The vector output by one-hot encoder 362 is input to an initial stage 364 consisting of a fully connected layer 366 followed by a ReLU layer 368. The outputs of ReLU layer 368 are input to a second stage 370 consisting of a fully connected layer 372 followed by a ReLU layer 374. In accordance with one embodiment, one hundred twenty-eight values are output from ReLU layer 368 to second stage 370.

During training, the output values of max pooling layer 340 of fourth stage 316 pass through a dropout layer 342 between fourth stage 316 and a final stage 380. Dropout layer 342 helps to prevent overfitting the neural network to the spectral data. When neural network 300 is used in production, dropout layer 342 is not present and all of the output values of max pooling layer 340 are provided to final stage 380.

Final stage 380 also receives output values from second stage 352 and second stage 370. Final stage 380 includes a fully connected layer 382, followed by a ReLU layer 384 that is followed by a dropout layer 386 and then a fully connected layer 388. Note that dropout layer 386 is only present during training to avoid overfitting to the input training values. Dropout layer 386 is not present when neural network is being used. Final stage 380 produces an organic percentage 390 and a moisture content 392.

As shown above, neural network 300 identifies both the organic percentage and the moisture content at the same time. Applicants have discovered that neural network 300 provides more accurate results for both the organic percentage and the moisture content when these values are determined at the same time rather than training two different neural networks: one for organic percentage and another for moisture content. Because of this the present embodiments improve the computing system by not only providing more accurate organic matter and moisture content predictions but also by using only a single neural network instead of two separate neural networks when making these predictions. This reduces the number of parameters that must be trained for the neural networks and the amount of processing that must be performed to predict both the organic matter percentage and the moisture content.

Although neural network 300 is shown as using geographic area 308, temperature value 304 and humidity value 306 in the embodiment of FIG. 3, in other embodiments neural network 300 is constructed to use only one of these three values or two of these three values. For example, in one embodiment, geographic area 308, one-hot encoder 362, first stage 364 and second stage 370 are not present in the neural network while the remaining elements of neural network 300 are present. In another embodiment, humidity value 306, geographic area 308, one-hot encoder 362, first stage 364 and second stage 370 are not present in the neural network while the remaining elements of neural network 300 are present. In such embodiments, initial stage 350 receives only temperature value 304. In a still further embodiment, temperature value 304, geographic area 308, one-hot encoder 362, first stage 364 and second stage 370 are not present in the neural network while the remaining elements of neural network 300 are present. In such embodiments, initial stage 350 receives only humidity value 306.

In accordance with one embodiment, neural network 300 is trained using spectral analyses of soil samples together with the corresponding ambient temperature, ambient humidity and geographic area. In order to increase the available data, multiple spectral analyses were performed on some of the samples to determine variances in the spectral data. The variances were then used to generate synthetic spectral graphs for each soil sample. The synthetic spectral values were then added to the actual spectral analyses performed on soil samples to provide additional training samples.

Figure 4:
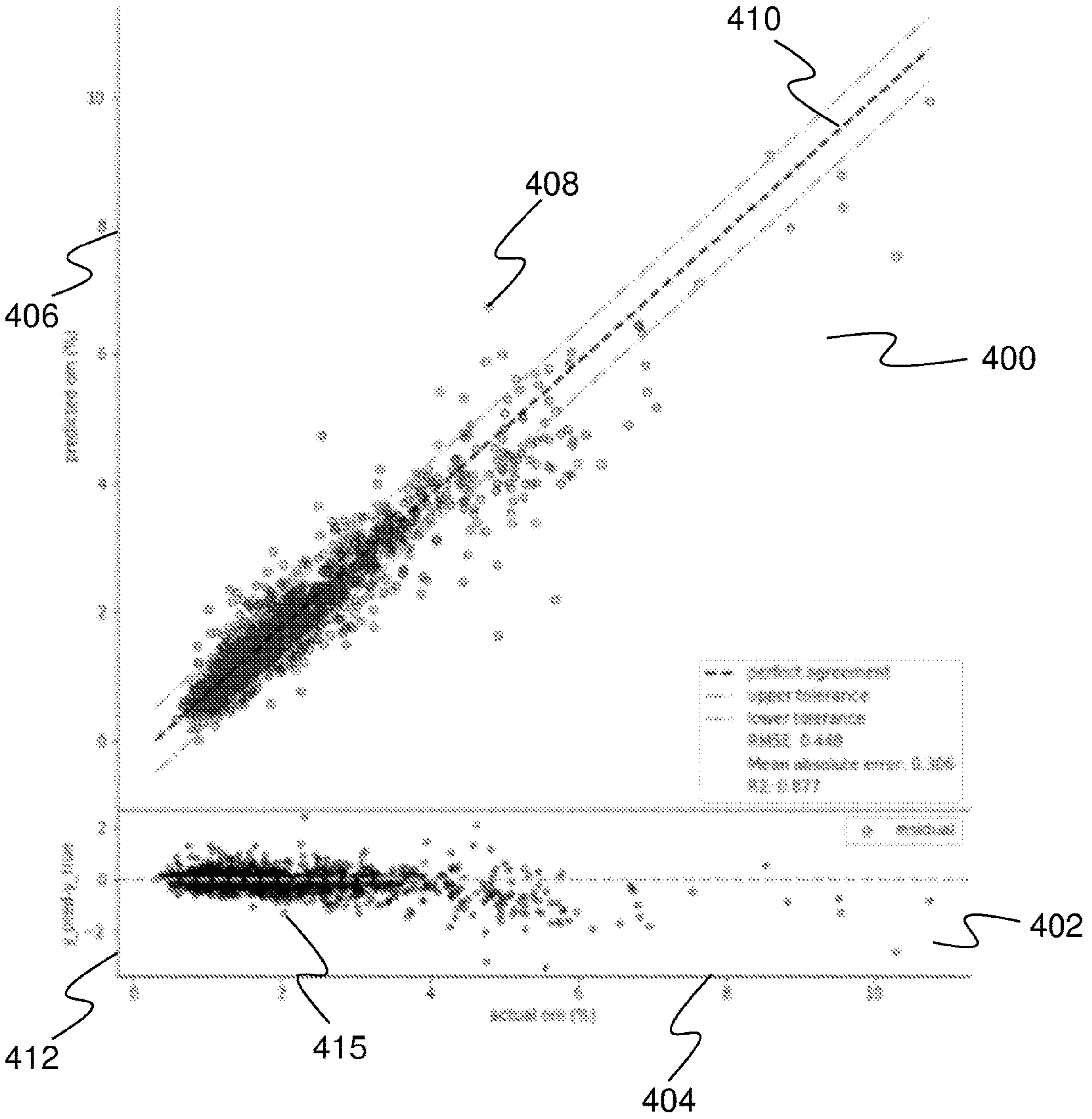
FIG. 4 provides a scatter plot of actual organic matter percentages versus organic matter percentages predicted by prior art neural networks.
Figure 5:
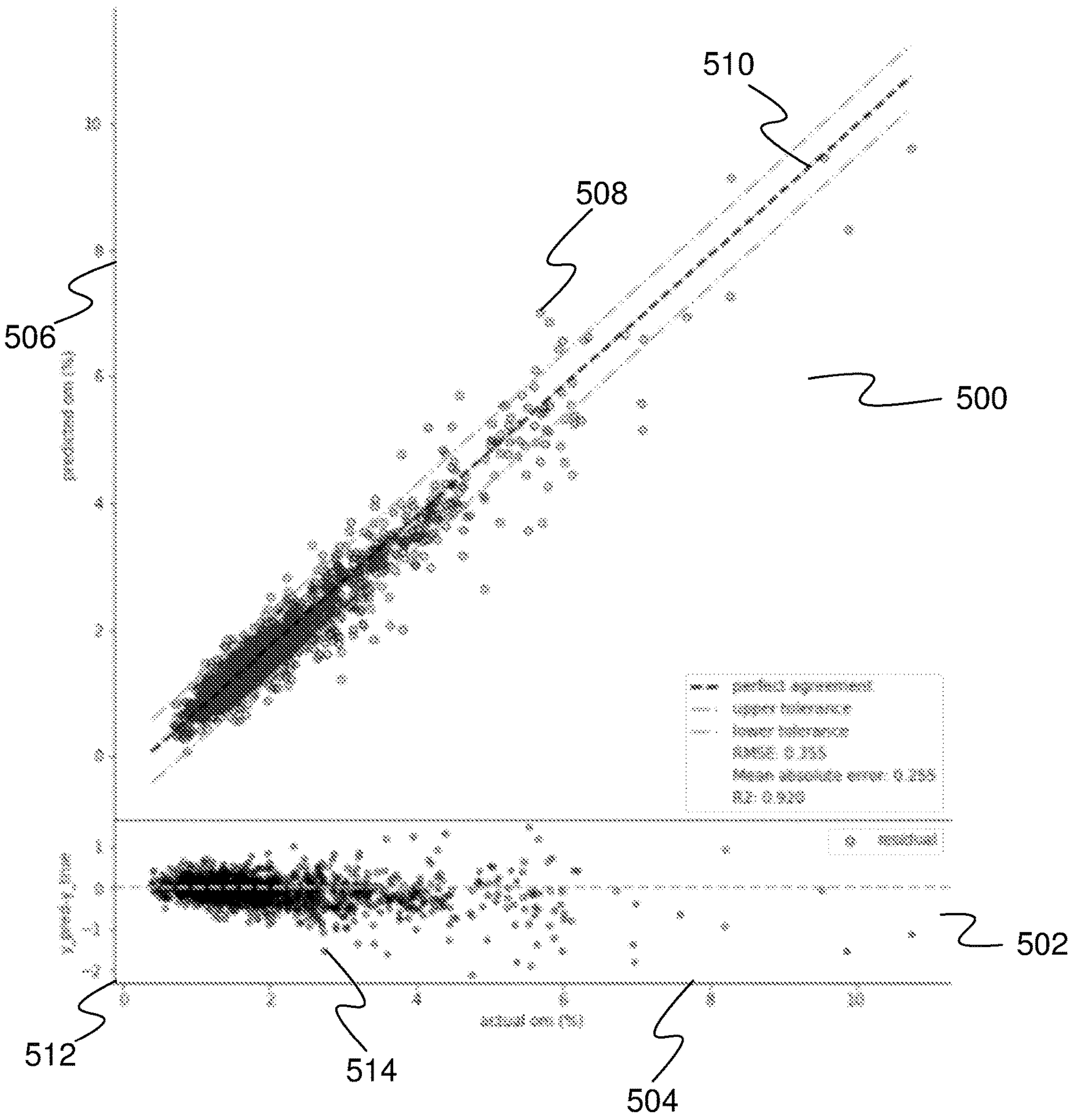
FIG. 5 provides a scatter plot of actual organic matter percentages versus organic matter percentages predicted by the improved neural network of one embodiment.

The application of the geographic area, the temperature value and the humidity value improved the ability of the neural network to predict the organic matter percentage and the moisture content. FIGS. 4 and 5 show graphs depicting the performance of an organic matter measurement system before and after the inclusion of geographic area, ambient temperature and ambient humidity, respectively. In FIG. 4, two graphs 400 and 502 are shown. Graph 400 depicts actual organic matter percentage on horizontal axis 404 and the organic matter percentage predicted without the geographic area, ambient temperature or ambient humidity on vertical axis 406. Each circle shown in graph 400, such as circle 408, is a separate organic matter percentage prediction and the ideal prediction is shown as line 410. Graph 402 shows the actual organic matter percentage on horizontal axis 404 and organic matter percentage prediction error along vertical axis 412. Each circle in graph 402, such as circle 414, indicates the error in a respective prediction of graph 400. The predictions in graph 400 have a Root-Mean Square Error (RMSE) of 0.448. Note that the organic matter percentages predictions shown are determined using real data that was not used to train the neural network.

In FIG. 5, two graphs 500 and 502 are shown. Graph 500 depicts actual organic matter percentage on horizontal axis 504 and the organic matter percentage predicted with the geographic area, ambient temperature or ambient humidity on vertical axis 506. Each circle shown in graph 500, such as circle 508, is a separate organic matter percentage prediction and the ideal prediction is shown as line 510. Graph 502 shows the actual organic matter percentage on horizontal axis 504 and organic matter percentage prediction error along vertical axis 512. Each circle in graph 502, such as circle 514, indicates the error in a respective prediction of graph 500. The predictions in graph 500 have a Root-Mean Square Error (RMSE) of 0.355. Note that the organic matter percentages shown are determined using real data that was not used to train the neural network.

Thus, as shown by the graphs of FIGS. 4 and 5, making organic matter percentage predictions while taking into account geographic area, ambient temperature and ambient humidity improves spectral organic matter percentage prediction technology by reducing the amount of error in the predictions. For example, in the data of FIGS. 4 and 5, the RMSE was reduced from 0.488 to 0.355 by including geographic area, ambient temperature and ambient humidity.

Figure 6:
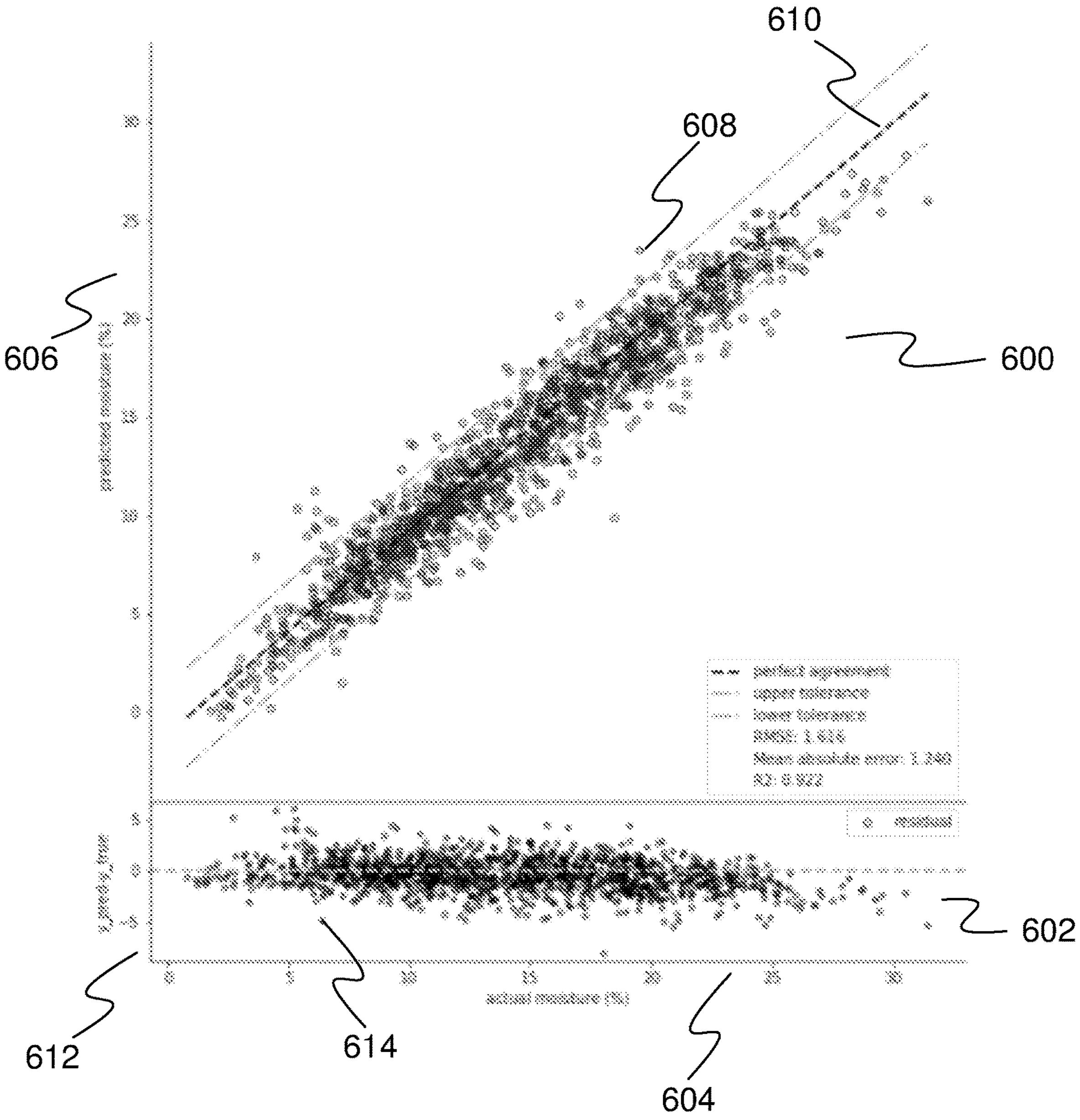
FIG. 6 provides a scatter plot of actual moisture content versus moisture content predicted by prior art neural networks.
Figure 7:
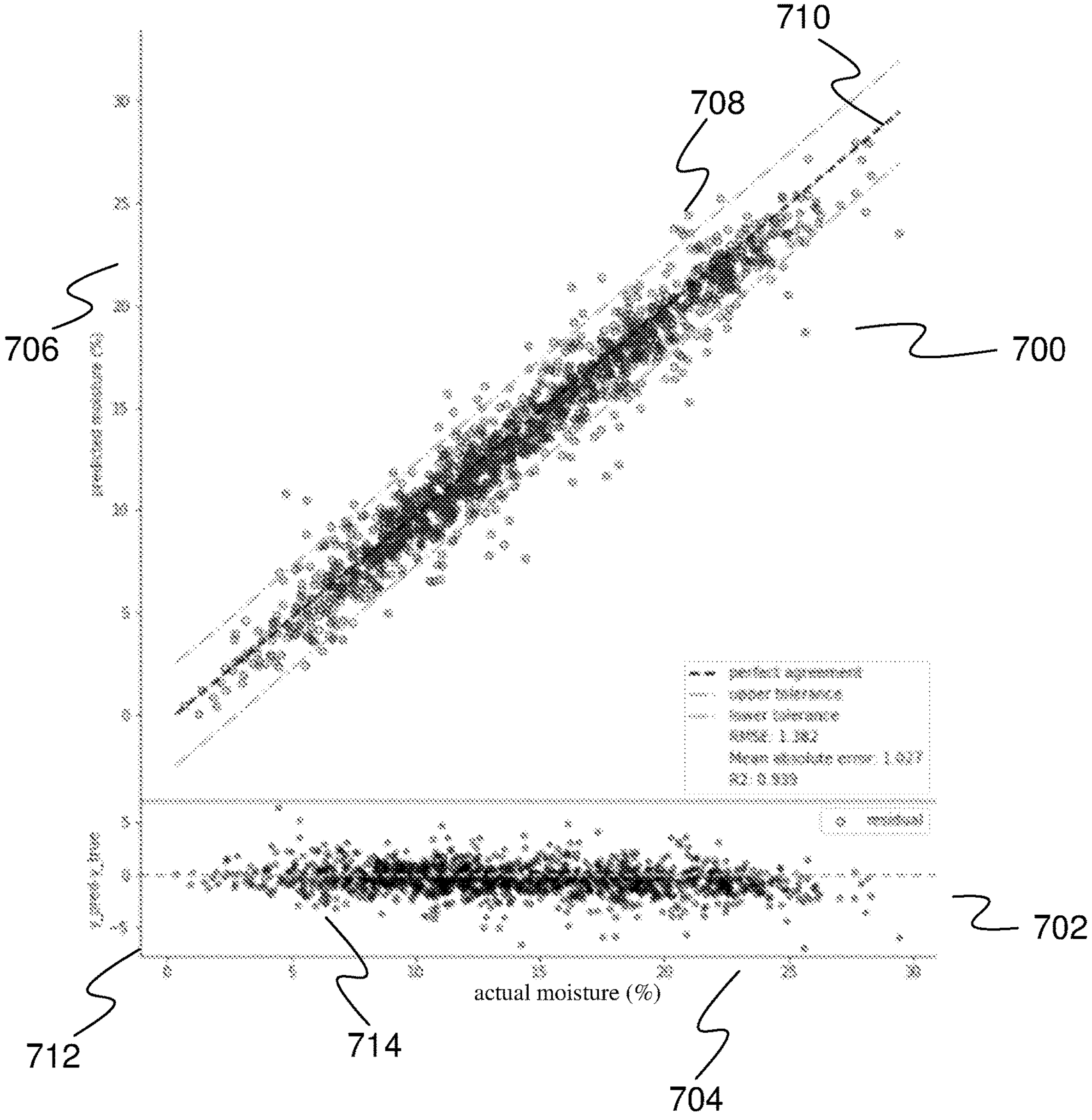
FIG. 7 provides a scatter plot of actual moisture content versus moisture content predicted by the improved neural network of one embodiment.

FIGS. 6 and 7 show graphs depicting the performance of a moisture content measurement system before and after the inclusion of geographic area, ambient temperature and ambient humidity, respectively. In FIG. 6, two graphs 600 and 602 are shown. Graph 600 depicts actual moisture content on horizontal axis 604 and the moisture content predicted without the geographic area, ambient temperature or ambient humidity on vertical axis 606. Each circle shown in graph 600, such as circle 608, is a separate moisture content prediction and the ideal prediction is shown as line 610. Graph 602 shows the actual moisture content on horizontal axis 604 and moisture content prediction error along vertical axis 612. Each circle in graph 602, such as circle 614, indicates the error in a respective prediction of graph 600. The predictions in graph 600 have a Root-Mean Square Error (RMSE) of 1.616. Note that the moisture content percentages shown are determined using real data that was not used to train the neural network.

In FIG. 7, two graphs 700 and 702 are shown. Graph 700 depicts actual moisture content on horizontal axis 704 and the moisture content predicted with the geographic area, ambient temperature or ambient humidity on vertical axis 706. Each circle shown in graph 700, such as circle 708, is a separate moisture content prediction and the ideal prediction is shown as line 710. Graph 702 shows the actual moisture content on horizontal axis 704 and moisture content prediction error along vertical axis 712. Each circle in graph 702, such as circle 714, indicates the error in a respective prediction of graph 700. The predictions in graph 700 have a Root-Mean Square Error (RMSE) of 1.382. Note that the moisture content percentages shown are determined using real data that was not used to train the neural network.

Thus, as shown by the graphs of FIGS. 6 and 7, making moisture content predictions while taking into account geographic area, ambient temperature and ambient humidity improves spectral moisture content prediction technology by reducing the amount of error in the predictions. For example, in the data of FIGS. 6 and 7, the RMSE was reduced from 1.616 to 1.382 by including geographic area, ambient temperature and ambient humidity.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A method of improving the ability of a neural network system to correctly predict the percentage of organic matter in an unprocessed soil sample, the method comprising:

placing the unprocessed soil sample in a spectroradiometer;

recording a value for a spectral band generated by the spectroradiometer from the unprocessed soil sample;

recording an ambient humidity level for air proximate the spectroradiometer;

recording an ambient temperature value for air proximate the spectroradiometer;

inputting the value for the spectral band to the neural network system that predicts a percentage of organic matter in the unprocessed soil sample using values of spectral bands; and improving the ability of the neural network system to correctly predict the percentage of organic matter in the soil sample by further inputting the ambient humidity level to the neural network system wherein the humidity level indicates an amount of ambient moisture present proximate the spectroradiometer when the value for the spectral band was identified, and further inputting the ambient temperature value to the system, and the neural network system uses the ambient humidity level and the ambient temperature value when predicting the percentage of organic matter.

2. The method of claim 1 wherein the system further predicts a moisture content of the soil sample using the values of the spectral bands and the method further comprises improving the ability of the system to correctly predict the moisture content of the soil sample by inputting the humidity level to the system.

3. The method of claim 2 further improving the ability of the system to correctly predict the moisture content and organic matter of the soil sample by further inputting a geographic area to the system wherein the geographic area describes a location where the soil sample was taken from.

4. The method of claim 1 further improving the ability of the system to correctly predict the percentage of organic matter in the soil sample by further inputting a geographic area to the system wherein the geographic area describes a location where the soil sample was taken from.

5. The method of claim 1 further comprising inputting a plurality of respective values of different spectral bands to the system.

6. The method of claim 1 wherein the system comprises a convolution neural network model.

7. The method of claim 1, wherein the unprocessed soil sample has not been ground or dried.

8. A system comprising:

a spectroradiometer configured to generate spectral band values from an unprocessed soil sample;

a memory containing parameters representing a neural network;

a processor using the parameters of the neural network stored in the memory to form the neural network such that the neural network comprises:

at least one spectral stage receiving spectral band values determined from a soil sample using the spectroradiometer and providing spectral stage outputs based on the spectral band values;

at least one ambient stage receiving an ambient humidity value representing ambient moisture present proximate the spectroradiometer when the spectral band values were determined and providing ambient stage outputs based on the ambient humidity value, the at least one ambient stage further receiving ambient temperature values representing a temperature present proximate the spectroradiometer when the spectral bands were determined; and a final stage receiving both the spectral stage outputs and the ambient stage outputs and indicating an organic matter percentage for the soil sample based on the spectral stage outputs and the ambient stage outputs wherein the spectral band values determined from the unprocessed soil sample are determined without processing the soil sample before determining the spectral values.

9. The system of claim 8 further comprising at least one geographic stage that receives a geographic area where the soil sample was obtained from and provides geographic outputs and wherein the final stage receives the geographic outputs.

10. The system of claim 8 wherein the final stage further indicates a moisture content of the soil sample.

11. The system of claim 8 wherein the at least one spectral stage comprises a convolution layer.

12. The system of claim 8, wherein the soil sample comprises a soil sample that has not been ground or dried before determining the spectral values.

13. A method for estimating a percentage of organic material in an unprocessed soil sample comprising:

placing the unprocessed soil sample in a spectroradiometer;

recording values for spectral bands generated by the spectroradiometer from the unprocessed soil sample;

recording a humidity level for air proximate the spectroradiometer;

recording a temperature value for air proximate the spectroradiometer;

providing the recorded values for the spectral bands and the recorded value for the humidity level to a processing unit; and providing the temperature value to the processing unit when providing the recorded values for the spectral bands and the recorded value for the humidity level to the processing unit;

the processing unit executing a neural network that uses the values for the spectral bands, the humidity level, and the temperature value to provide the percentage of organic material in the unprocessed soil sample.

14. The method of claim 13 further comprising providing an area where the soil sample was obtained from to the processing unit when providing the recorded values for the spectral bands and the recorded value for the humidity level to the processing unit; and wherein the neural network uses the area where the soil sample was obtained with the values for the spectral bands and the humidity level when providing the percentage of organic material in the unprocessed soil sample.

15. The method of claim 13 wherein the neural network uses both the values for the spectral bands and the humidity level to provide a moisture content of the unprocessed soil sample.

16. The method of claim 13, wherein the unprocessed soil sample has not been ground or dried.

* * * * *